United States Patent [19]

Schmitt et al.

[11] 4,067,853
[45] * Jan. 10, 1978

[54] COMPOSITIONS OF BISHYDROXYSUBSTITUTEDARY DI ACRYLATES FOR PROSTHODONTIA

[75] Inventors: Werner Schmitt; Robert Purrmann, both of Starnberg; Peter Jochum; Wolf Dieter Zahler, both of Hechendorf, all of Germany

[73] Assignee: ESPE Fabrik pharmazeutischer Praparate GmbH, Germany

[ * ] Notice: The portion of the term of this patent subsequent to Dec. 2, 1992, has been disclaimed.

[21] Appl. No.: 601,689

[22] Filed: Aug. 1, 1975

Related U.S. Application Data

[63] Continuation-in-part of Ser. No. 276,334, July 31, 1972, Pat. No. 3,923,740, which is a continuation of Ser. No. 824,702, May 14, 1969, abandoned.

[51] Int. Cl.$^2$ .................. C08F 20/38; C08F 20/30
[52] U.S. Cl. .................. 260/47 UA; 106/35; 260/42.18; 260/79.3 MU; 260/DIG. 36; 526/72
[58] Field of Search .... 260/47 UA, 47 UP, 79.3 MU; 106/35; 526/326

[56] References Cited

U.S. PATENT DOCUMENTS

| | | | |
|---|---|---|---|
| 2,456,318 | 11/1948 | Ramier | 260/89.5 R |
| 2,830,078 | 4/1958 | Fekete | 260/89.5 R |
| 2,890,202 | 6/1959 | Parker | 260/47 |
| 3,179,623 | 4/1965 | Bowen | 260/47 |
| 3,538,149 | 11/1970 | Hoffman | 260/486 R |
| 3,810,938 | 5/1974 | Schmitt | 260/486 R |

FOREIGN PATENT DOCUMENTS

| | | | |
|---|---|---|---|
| 7,015,640 | 1970 | Japan | 260/47 UA |
| 1,089,867 | 1967 | United Kingdom | 260/486 |

Primary Examiner—Christopher A. Henderson, Jr.
Attorney, Agent, or Firm—Nolte and Nolte

[57] ABSTRACT

Superior artificial teeth, dentures, other dental replacement parts and dental prosthetic articles and devices, which exhibit high abrasion resistance, stability to moisture and which do not undergo volume changes, are obtained by polymerization of a compound of the formula

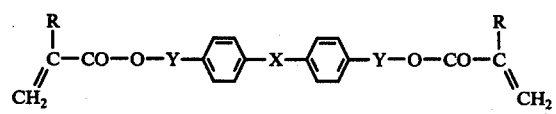

in which R is H or -CH$_3$, X is an alkylidene or the -SO$_2$- group, Y is an oxyalkylene group having between 2 and 5 carbon atoms, or an alkylidene group having between 1 and 5 carbon atoms. In some instances, the polymerization is carried out in the presence of a filler.

12 Claims, No Drawings

COMPOSITIONS OF BISHYDROXYSUBSTITUTEDARY DI ACRYLATES FOR PROSTHODONTIA

This is a continuation-in-part of application Ser. No. 276,334, filed July 31, 1972, now U.S. Pat. No. 3,923,740 which, in turn, is a continuation of application Ser. No. 824,702, filed May 14, 1969, now abandoned.

This invention relates to novel, improved artificial dentures. The term "artificial dentures" as used in the present application includes artificial teeth, dentures, other dental replacement parts and dental prosthetic articles and devices in general.

For the preparation of dental fillings, crowns, bridges and replacement parts, in addition to gold and porcelain, also some synthetic substances have been used, such as, in particular, polymers prepared from easily polymerizable unsaturated compounds of the olefinic type. These synthetic substances offer substantial advantages as compared with fillings and replacement parts made of gold and porcelain, because they are satisfactory in appearance, and because they are not sensitive to breakage as porcelain. It is also possible with these synthetic substances, to match more easily the particular color of teeth of different individuals.

In the last thirty years, polymethacrylate compositions have been used in dentistry for the purpose of preparing dental fillings, crowns, artificial teeth and in repair work. The polymerization of the monomer methyl methacrylate has been conducted, if possible, by applying heat so that a good degree of polymerization is achieved. More recently, other synthetic substances, such as for instance, the newly developed polyamides, polycarbonates and above all, the great number of esters of methacrylic acid which have been synthesized in the last ten years, have also been investigated for their applicability in dental work and they have been recommended to some extent. However, every effort to substitute methyl methacrylate with other acrylic or methacrylic acid derivatives, have given essentially unsatisfactory results and the dental industry always goes back to using methyl methacrylate. The latter substance still today dominates the field just as much as in the past.

When teeth fillings have to be prepared, the polymerization may only be conducted at room temperature or at body temperature. The main drawback of this cold polymerization is that a small portion of the methyl methacrylate remains unpolymerized. It has been found that these residues of monomer gradually diffuse out from the fillings and cause damage mostly to the pulp of the teeth. For this reason, methyl methacrylate fillings, in general, are used only in the case of dead teeth.

For the purpose of improving the mechanical properties, particularly the abrasion resistance of the synthetic substances, some bifunctional esters of methacrylic acid have also been used, which have given three-dimensional cross-linked products. The application of one of these bifunctional esters of methacrylic acid to the preparation of dental fillings has been described in U.S. Pat. No. 3,066,112, where the ester of methacrylic acid is prepared by reaction of phenols, specifically, isopropylidenediphenol with glycidyl methacrylate. The bifunctional methacrylic acid esters so obtained, must be used together with a filler consisting mainly of silica and the filler is pretreated with a vinylsilane compound.

The polymers described in the preceeding paragraph, prepared by the conventional polymerization of bifunctional methacrylic acid esters, that is, esters prepared by reaction of bisphenol with glycidyl methacrylate, are not completely inert to moisture, and in the presence of water or saliva, the mechanical strength is decreased and volume changes occur.

Also the bifunctional esters of methacrylic acid of the type of glycerine esters have been investigated but, in accordance with the U.S. patent mentioned above, they are too highly viscous and must be mixed with methyl methacrylate or ethyleneglycol dimethacrylate or tetramethyleneglycol dimethacrylate or other suitable low molecular weight reactive extenders, for the purpose of lowering the viscosity and making sure that the ingredients may be successfully used in dentistry. The result of this combination, however, is that also with these masses of bifunctional esters of methacrylic acid, it is necessary to add low molecular weight acrylic esters of similar substances. The drawback, as already discussed above, is that residues of unpolymerized monomeric materials of these low molecular weight extenders remain, which are toxic to the pulp of the teeth.

An object of this invention is to provide materials of high stability and superior abrasion resistance for "artificial dentures," as that expression is defined hereinabove. Further, the artificial dentures which are an object of this invention exhibit practically no tendency to absorb water and undergo essentially no change in volume during the polymerization process and under the conditions existing in the mouth.

The crux of this invention resides in the finding that, surprisingly, superior artificial dentures are obtained if the monomer being polymerized is a bifunctional monomer consisting of a diester of acrylic acid with a dihydroxy compound, of general formula I.

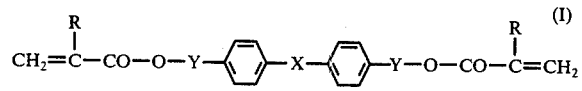

In formula I, R stands for a hydrogen atom or a methyl group, X represents an alkylidene or a —SO$_2$— group, and Y represents an oxyalkylene group having between 2 and 5 carbon atoms or an alkylidene group containing between 1 and 5 carbon atoms.

According to the preferred embodiments of the invention, X is the isopropylidene group and Y is an oxyalkylene group having between 2 and 3 carbon atoms or an ethylidene group which, in some cases, may be substituted.

In general, the methacrylic esters are superior to the acrylic esters, because they are less susceptible to hydrolysis and because they exhibit better mechanical properties. Particularly suitable are the bifunctional methacrylic acid esters of diols derived from p,p'-dihydroxy-diphenylalkanes and p,p'-dihydroxy-diphenylsulfone. These diols, for example, may be prepared by reaction of the aforementioned bis-phenols with epoxides or halohydrins. The bis-hydroxy-ethoxy-and bis-hydroxy-propoxy - derivatives of diphenylalkanes, such as for instance, 2,2-diphenylpropane, 2,2-diphenylbutane or 1,1-diphenylcyclohexane are very advantageous.

The benzene rings of the dihydroxy compound of formula I may also be substituted with lower alkyl or lower alkoxy groups, that is, with groups having between 1 and 4 carbon atoms, for instance, a methyl or a methoxy group. Substitution of the benzene rings has no effect on the ability to form esters with acrylic or methacrylic acid, nor does it affect the properties of the polymer.

According to a specific particularly suitable embodiment of this invention, the compound being polymerized has the formula II below:

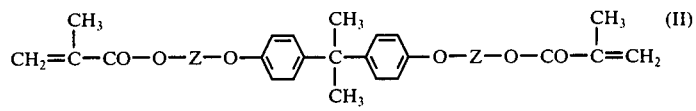

in which Z is an alkylene group having between 2 and 5 carbon atoms. When jacket crowns and anterior portions are to be manufactured by hot polymerization, the diester of methacrylic acid of formula III below has proved to be advantageous:

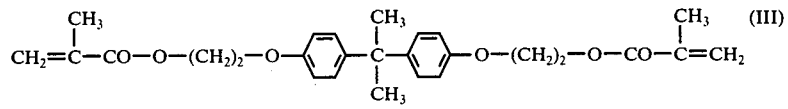

The bifunctional starting materials, in general, are liquids of relatively low viscosity or relatively low-melting substances. They are prepared, in general, according to conventional methods of esterification and transesterification. For instance, the diols may be directly esterified with methacrylic acid in the presence of known esterification catalysts, such as, for instance, p-toluenesulfonic acid. The preparation of the bifunctional monomers may also be conveniently conducted by transesterification of methacrylic acid alkyl esters, for instance, the methyl ester, in the presence of conventional basic or acid catalysts. Particularly advantageous is the preparation of the esters by reaction of reactive derivatives of acrylic or methacrylic acid, such as the halide or the anhydride. The addition of a dehydrating agent may also be advantageous. In all the operation, it is preferable to operate in an atmosphere of an inert gas and to use a polymerization inhibitor, such as, for instance, a 2,6-disubstituted phenol.

The polymerization of the bifunctional esters is conducted in conventional fashion in the presence of substances capable of forming free radicals, such as peroxides or azocarboxylic acid nitriles. As the peroxides, benzoylperoxide, lauroyl peroxide, mono-t-butyl permaleate or t-butyl hydroperoxide, may be used. The azocarboxylic acid nitrile may be, among others, azoisobutyronitrile. For the preparation of replacement parts, to be used in repair work, the polymerization is carried out with lauroyl peroxide by heating the mass in a mold for a few hours at 90° C or at temperatures up to 160° C for a short period of time. It is preferable to conduct the polymerization at 120°-160° C in a current of hot air, for the purpose of achieving the highest possible degree of cross-linking.

For the preparation of dental fillings in the mouth, substances capable of acting as initiators at room temperature, particularly the known redox-systems are used. With these catalysts, the bifunctional esters in accordance with this invention may be polymerized in the course of a few minutes at room temperature or at body temperature. It is preferable to use substances which have no tendency to discolor, such as for instance, known sulfone derivatives, such as hydroxy or aminosulfones. It is also possible to use soluble salts of sulfonic acids with tertiary amines or quaternary ammonium bases, particularly in combination with peroxides. Suitable catalysts are also substances containing the so-called active —CH— group, such as 5-monosubstituted barbituric acid derivatives, or betadiketones, in combination with known cocatalysts, for instance, traces of heavy metals and chlorine ions. The known system of benzoyl peroxide together with N,N-dimethyl-p-toluidine is satisfactory as a catalyst to cause rapid polymerization at room temperature; the resulting polymers, however, are but little stable to discoloration. When using redox-systems, it may be advisable to use a cover against oxygen of the air, because the latter has a well known inhibitory effect.

One advantage of the artificial dentures prepared in accordance with this invention is that it is not necessary to add highly fluid low-molecular weight acrylic or methacrylic esters during the polymerization. If the substances are solid at room temperature, they as a rule have a low melting point, so that the manufacture of the artificial dentures by hot polymerization in molds may be easily conducted at temperatures above the melting points of the substances.

The polymerization as a rule is conducted in the presence of fillers. Particularly advantageous as fillers are, among others, finely divided polymethyl methacrylate, which is available in commerce in the form of small beads, glass fibers, quartz fibers, quartz powder, alumina and silicates.

Another advantage of this invention is that the compounds of formula I polymerize well and even if small amounts of the unpolymerized monomers remain, no risk of damage to the pulp of the teeth exists. This is in direct contrast with articles prepared from methyl methacrylate. The reason is that the relatively high molecular weight substances exhibit only a very small tendency to diffuse out from the polymerized material.

Another advantage of the dental fillings and replacement parts prepared in accordance with this invention, as compared with other fillings and prosthetic articles known in the art, is that no changes in dimensions occur, even on prolonged standings in the mouth. It is of utmost importance in the use of synthetic substances in dental medicine, that the substances exhibit practically no tendency to absorb water at 36° C., because otherwise, changes in dimensions unavoidably occur, as a result of the swelling with moisture. If the material absorbs water, the preparations may detach or the jacket crowns may crack. In the case of pure methyl methacrylate, it is known in the literature that it swells by about 1% under the conditions existing in the human mouth. (See the book by Paul Weikart entitled "Science of Industrial Materials for Dentists," published by Carl Hanser-Verlag, Munich, 1966, at p. 162.)

Another significant advantage with the compounds of this invention, is that the ester functional groups are stable to hydrolysis. Also the polymers prepared according to this invention, exhibit a considerably superior abrasion resistance as compared with commercially available polymerization products, such as for instance, polymethacrylate.

The following examples are set forth below for the purpose of better illustration of the invention.

EXAMPLE 1

The diester, 2,2-bis-(p-($\beta$-hydroxy-ethoxy-)phenyl)-propane-dimethacrylate, was prepared by transesterification of 2,2-bis-(p-($\beta$-hydroxy-ethoxy-)phenyl)-propane and methylmethacrylate, in analogy with the process described by John V. Schmitz in J.Am.Chem.Soc. 77, 194 (1955) for the preparation of tetraethyleneglycoldimethacrylate. The substance, recrystallized from cyclohexane, melted at 44°–45° C.

Preparation of jacket crowns

A paste was prepared from the diester described above with 80% of a mixture of polymethyl methacrylate, the bead polymer stained to imitate natural teeth, and lauroyl peroxide, in the ratio by weight of 100:1, at 50° C. The paste was placed in suitable molds for the preparation of jacket crowns and after heating 15 hours at 90° C., the crowns were removed from the molds and allowed to set.

EXAMPLE 2

Preparation of artificial teeth

The diester described in Example 1, in the amount of 10 grams, was mixed with 5 mgs. of a white pigment, 8 mgs. of a yellow pigment and 100 mgs. of benzoyl peroxide. The material was heated at 160° C. for 30 minutes in suitable molds for the preparation of artificial teeth.

EXAMPLE 3

Preparation of Jacket Crowns

A paste was prepared from 20 grams of the diester of Example 1 and 6.5 grams of quartz fibers. Small portions of this paste were mixed with the bead polymer from methyl methacrylate, which was colored with the usual shades for jacket crowns and which contained 0.8% of lauroyl peroxide. The proportion was about 3:2 by weight. Then the particular shades corresponding to the shades of natural teeth were applied in layers on a model. After depositing each layer, the material was heated for a short time in a current of hot air at 150° C. and after completion of the crown, polymerization was completed at 160° C. for 10 minutes.

EXAMPLE 4

Preparation of Anterior Portions of Bridges

The mixture described in Example 3 from the diester of methacrylic acid and quartz fibers is suitable also for the preparation of the anterior portions of bridges made of noble metals. The mixture was mixed with the bead polymer from methyl methacrylate and a paste was obtained. The paste was deposited in layers in the manner described in Example 3, by the conventional procedure of depositing the material on the anterior portion of the frame of the bridge. The material was finally polymerized by heating.

EXAMPLE 5

The diester, 2,2-bis-(p-($\beta$-hydroxy-ethoxy-)phenyl)-propane-diacrylate, was prepared by transesterification of 2,2-bis-(p-($\beta$-hydroxy-ethoxy-)phenyl)-propane with methyl acrylate, in accordance with the procedure described in Example 1. The substance was used for the preparation of artificial teeth in accordance with the procedure described in Example 2, by polymerization in molds.

EXAMPLE 6

The compound 2,2-bis-(p-($\beta$-hydroxy-ethoxy-)phenyl)-sulfone was transesterified with methyl methacrylate in accordance with the procedure of Example 1. The product, 2,2-bis(p-($\beta$-hydroxy-ethoxy-)phenyl)-sulfone-dimethacrylate, recrystallized from benzene-cydohexane in the ratio of 1:1, had a melting point of 100°–102°.

The polymerization was conducted by mixing with 0.5% of lauroyl peroxide, with small amounts of pigments, in molds, by heating at 160° C. for a short period of time.

EXAMPLE 7

A fluid mixture was obtained by dissolving 3 parts of the compound of Example 1 with 1 part of hexanediol-1,6-dimethacrylate, at 30° C. A paste was then formed from this mixture, with 70% by weight of thin quartz fibers, 10% by weight of tricalcium phosphate, 1% by weight of N,N-dimethyl-p-toluidine, 100 parts per million of a yellow pigment and 40 parts per million of a red pigment. This paste, 1 gram, was mixed with 15 mg. of a powder consisting of 20% of benzoyl peroxide and 80% of gypsum. The mixture was placed in a cavity, and after a few minutes at room temperature, polymerization occurred, as evidenced by the fact that the material hardened.

EXAMPLE 8

A slimy paste was prepared from 56.8 grams of 2,2-bis(p-($\alpha$-hydroxyethyl-)phenyl)-propane which has been prepared from 2,2-bis-(p-acetyl-phenyl)-propane, by reduction with $NaBH_4$, together with 140 ml. of benzene and 100 ml. of triethylamine. Under cooling at $-5°$ C., there was added dropwise 63 grams of methacrylic acid chloride and the mixture was kept under stirring one additional hour. After addition of 400 ml. of water, the benzene layer was separated, washed with dilute sulfuric acid sodium hydroxide and then with alumina.

After removing the solvent in vacuo, the product 2,2-bis-(p-($\alpha$-hydroxyethyl-)phenyl)-propane-dimethacrylate, 42.5 grams was obtained, in the form of a colorless liquid, which had a double bond equivalent of 208. The substance, in cyclohexane, exhibited two ultraviolet maxima in the region of 223 and 263 m$\mu$. ($\epsilon$ mol. 20 250 and 1210 respectively.)

Preparation of dental fillings

Dental fillings were prepared by dissolving N,N-dimethyl-p-toluidine in the substance prepared above, to obtain a 2% solution, adding the fillers as in Example 7 and kneading. After addition of 1% of benzoyl peroxide, the material set in about 2 minutes and the polymerization was complete essentially in 6 minutes.

EXAMPLE 9

Preparation of artificial teeth

The material described in Example 1, in the amount of 10 grams, was used as in Example 2, but 50 mgs. of azo-isobutryonitrile were used as the catalyst for the polymerization instead of 100 mg. of benzoyl peroxide. Artificial teeth of very good quality were obtained in the mold after the polymerization was complete.

EXAMPLE 10

Methacrylic acid, 130 grams, was esterified with 167 grams of the diastereisomer mixture of 2,2-bis-(p-($\beta$-hydroxy-propoxy-)phenyl)-propane in 300 ml. of benzene, 6.8 grams of p-toluene sulfonic acid, and 0.3 gram of picric acid. The water formed during the reaction was removed with boiling benzene over a period of 200 hours. The product was purified by treatment with sodium hydroxide, water and alumina in the usual manner. After drying and removal of the solvent in vacuo, a colorless oil was obtained, 102 grams, which exhibited a viscosity of 46 poises at 25° C. The substance, in chloroform, exhibited two ultraviolet maxima, at 278 m$\mu$ and 285 m$\mu$ ($\epsilon$ mol. 3.680 and 3.310 respectively).

Preparation of teeth fillings

A 0.1% solution of dibutylphenyl-ethylamine hydrochloride in the substance prepared above, 2,2-bis-(p-($\beta$-hydroxypropoxy-)phenyl)-propane-dimethacrylate was prepared, and copper-propionyl-acetophenate, in the amount of 13 parts per million was added. A paste was then formed from 0.5 grams of this solution and 0.5 gram of a polymethyl methacrylate bead polymer, colored to imitate natural teeth. The latter contained 2% benzoyl peroxide and 1,3-dimethyl-5-isobutyl-barbituric acid. The reaction began after a few minutes and was essentially completed after about 10 minutes at 36° C.

EXAMPLE 11

To a mixture of 480 grams of sodium hydroxide, dissolved in 1.9 liters of water and 1.09 kg. of bis-phenol A, that is, 2,2-di-p-hydroxyphenyl-propane, dissolved in 1.2 liters of methanol, 1.14 kg. of 3-chloro-1-propanol was added dropwise at 65° C. and the mixture was heated at 80° C. for 5 hours. After cooling, the material was extracted with methylene chloride and the extract washed several times with sodium hydroxide. After drying and removal of the solvent, 1.350 kg. of a yellow oil was obtained, which recrystallized slowly. Dissolution and recrystallization from ethyl acetate gave 770 grams of 2,2-bis-(p-$\beta$-hydroxy-propoxy-)phenyl)-propane in the form of colorless crystals of melting point 48°–49° C.

The dihydroxy compound was transesterified with methyl methacrylate according to the procedure described in Example 1, whereby the bifunctional methacrylic acid ester was obtained. The substance was obtained as a colorless oil of viscosity 10 poises at 25° C. The substance in chloroform exhibited two ultraviolet maxima at 278 m$\mu$ and 285 m$\mu$ respectively ($\epsilon$ mol: 3.810 and 3.430 respectively).

Preparation of teeth fillings

A solution was prepared of 80 parts per million of dicyclohexyl-butylamine hydrochloride, and 2 parts per million of iron and copper in the form of their propionyl acetonphenate derivatives, in the substance prepared above. The solution, in the amount of 0.75 grams, was mixed with 0.3 grams of a bead polymer of polymethyl methacrylate, colored to imitate natural teeth and with 8 mg. of phenyl-hydroxymethyl sulfone and 10 mgs. of benzoyl peroxide. Hardening was complete in a few minutes.

EXAMPLE 12

To a mixture of 200 grams of sodium hydroxide, dissolved in 1 liter of water and 500 grams of p,p'dihydroxy-diphenylsulfone, dissolved in 520 ml. of methanol, were added 474 grams of 3-chloropropanol at 65° C. The mixture was heated at 80° C. for 7 hours. The crystals which separated on cooling, were purified by recrystallization from methanol-water in the ratio of 5:1. The yield was 290 grams of bis-(p-($\gamma$-hydroxy-propoxy)-phenyl)-sulfone of melting point 139°–141° C.

The esterification of this dihydroxy compound was conducted as in Example 10, with methacrylic acid and the product was purified in the usual fashion. The product was bis-(p-($\gamma$-hydroxy-propoxy)-phenyl)-sulfone-dimethacrylate, 95 grams, which recrystallized from methanol, melted at 78°–79° C.

The polymerization was conducted by mixing the diester with 0.6% of lauroyl peroxide together with the usual pigments. The product hardened after heating in suitable molds at 135° C., for one-half hour.

EXAMPLE 13

Bis-phenol A, that is 2,2-di(p-hydroxy-phenyl-)propane, was reacted in known manner with an excess of pentene - 1,2-oxide. The product, the mixture of diastereisomers, 2,2-bis-(p-($\beta$-hydroxy-pentoxy-)phenyl)-propane was obtained as a yellow-brown, semisolid mass, which was obtained as a colorless substance by distillation b.p.:192°–210° C/O .005 mm. The OH-equivalent was 207.

Esterification was conducted from 113 grams of the dihydroxy compound, with methacrylic acid in the manner as described in Example 10 and the product was purified in the usual manner. After evaporation of the solvent in vacuo, 84 grams of a colorless oil was obtained, which, in chloroform exhibited ultraviolet maxima in the region 278 m$\mu$ - 286 m$\mu$ ($\epsilon$ mol.: 3.720 and 3.330 respectively).

Preparation of teeth fillings

Polymerization was conducted from the diester, with isomer-free N,N-dimethyl-p-toluidine, in amount to form a 1.6% mixture, in the manner described in Example 8.

EXAMPLE 14 (Comparative examples)

Monomer and, therefrom, a polymer were made according to the procedure described in Example 3 of Canadian Patent No. 657,894. The resultant polymer was dark brown, almost black. Similarly, Example 4 of Canadian Pat. No. 657,894 was carried out. The polymer was light brown. It was found to be indeed necessary to use the elevated temperature schedules specified in Examples 3 and 4 of the Canadian patent. For purposes of comparison with the aforementioned polymeric products of the Canadian patent, the diesters of hereinabove Examples 1, 10 and 11 were polymerized under identical conditions as the substances of Examples 3 and 4 of the Canadian Patent. It was chosen the procedure as described by Parker in Example 3, namely after mixing in 3% benzoyl peroxide the test specimens were heated for one hour to 170° F ( = 77° C) and an additional hour at 250° F ( = 121° C).

The polymeric products of the diesters of hereinabove Examples 1, 10 and 11 were colorless and transparent. As described above the specimens of Examples posed for a period of 10 hours to the action of round brushes of 10 mm. diameter, driven by means of a motor and revolving at a speed of 60 revolutions per minute. The weight applied was 500 grams. After drying the weight loss was determined by weighing. The data of the experimental conditions and results of the tests, are summarized in Table I.

Table I

| Experiment No. | Monomer | Amount of the Additive, that is the filler, expressed in %, on the basis of the monomer | Conditions of Polymerization Temp. | Time in hrs. | Abrasion, in mgs. per 10 hrs. |
|---|---|---|---|---|---|
| 1 | Methylmethacrylate* | 250% Polymethylmethacrylate | 90° | 16 | 13.5 |
| 2 | Triethyleneglycol-*dimethacrylate | 100% Polymethylmethacrylate | 160° | 0.5 | 11.1 |
| 3 | Methylmethacrylate ("Plexiglas") | — | | | 9.2 |
| 4 | Compound of Example 1 of this application | 0.6% lauroyl peroxide | 160° | 0.5 | 0.3 |
| 5 | Compound of Example 1 of this application | 120% Polymethylmethacrylate "Plexigum M 353" (Rohm & Haas) 0.8% lauroyl peroxide | 90° | 16 | 3.3 |
| 6 | Compound of Example 1 of this application | 80% Polymethylmethacrylate "Plexigum M 353" (Rohm & Haas) 0.6% lauroyl peroxide | 160° | 0.5 | 0.9 |
| 7 | Compound of Example 1 of this application | 30% Polymethylmethacrylate "Plexigum M 353" (Rohm & Haas) 50% Quartz Fibers 0.8% lauroyl peroxide | 160° | 0.5 | 0.3 |
| 8 | Compound of Example 10 | 0.6% lauroyl peroxide | 135° | 0.5 | 1.3 |
| 9 | Compound of Example 11 | 0.6% lauroyl peroxide | 135° | 0.5 | 1.7 |
| 10 | Compound of Example 11 | 100% Polymethyl-methacrylate "Plexigum M 353" (Rohm & Haas) 0.6% lauroyl peroxide | 135° | 0.5 | 2.8 |

*Experiments 1 and 2 were conducted with commercially known substances 3 and 4 showed in contrast a dark brown or light brown appearance, respectively.

Determination of abrasion resistance

A significant advantage of the dental compositions prepared according to this invention resides in their superior resistance to abrasion. This was demonstrated by comparative experiments with commercially available substances. The comparative data were obtained by using, 2,2-bis-(p-($\beta$-hydroxyethoxy)phenyl-propane-dimethacrylate, that is the compound of Example 1 of this application, and the compounds of Examples 10 and 11, on the one hand, and preparations from either methyl methacrylate or triethyleneglycol dimethacrylate together with polymethyl methacrylate as the filler, as the commercially known product, on the other hand.

The abrasion resistance was determined from round test particles of 16 mm. diameter and 1.2 mm. thickness prepared in metallic molds, under the experimental conditions of polymerization set forth in Table I below. The particles were weighed. The abrasion resistance was determined by placing the particles in an aqueous suspension of pure precipitated calcium carbonate, Merck No. 2064, in the ratio by weight of water and calcium carbonate of 1:1. The particles were then ex- The substances prepared according to this invention exhibit superior behavior in the so-called "Hot-Cold Test." Hot-Cold experiments were conducted in such a manner as to imitate the conditions existing in the mouth following temperature changes, such as eating ice and drinking hot liquids. The change of the wedge breaking strength was used to determine the extent of deterioration of the tooth replacement parts.

The change in breaking strength was determined as follows. Cylindrical bodies of the test materials of 7.2 mm. diameter and 4 mm. height were prepared and were repeatedly and alternately immersed for 3 minute periods, in water at 10° C. and then in water at 60° C. The change of the wedge breaking strength including the depth of penetration were measured.

The determination of the breaking strength was conducted with testing apparatus sold under the trademark Frank 581. The samples were placed on a steel table and lifted against a wedge at a rate of 0.12 mm. per second. The surface of the hardened wedges formed an angle of 35° and the apex of the wedge had a cylindrical radius of curvature of 0.5 mm. At the breaking point of the particles, the pressure was read on a scale. The results are summarized in the following table.

Table II

| | Hot-Cold Experiments | | | | | |
|---|---|---|---|---|---|---|
| | Starting Materials | | | After 7,500 Changes | | |
| Material | Wedge breaking strength in kg. | Depth of penetration, 50 kg. (mm × 10$^{-2}$) | Depth of penetration, 100 kg. (mm × 10$^{-2}$) | Wedge Breaking strength in kgs. | Depth of penetration, 50 kg. (mm × 10$^{-2}$) | Depth of penetration, 100 kg. (mm × 10$^{-2}$) |
| 1 | 200 | 8 | 30 | 136 | 4 | 20 |
| 2 | 134 | 15 | 36 | 74 | 16 | — |
| 3 | 138 | 0 | 14 | 136 | 2 | 15 |
| 4 | 191 | 8 | 20 | 200 | 7 | 22 |

Materials tested:
Experiment    Commercial preparations; compositions and experimental conditions of polymerization

Table II-continued

| | Starting Materials | | | After 7,500 Changes | | |
|---|---|---|---|---|---|---|
| | | Hot-Cold Experiments | | | | |
| Material | Wedge breaking strength in kg. | Depth of penetration, 50 kg. (mm × 10⁻²) | Depth of penetration, 100 kg. (mm × 10⁻²) | Wedge Breaking strength in kgs. | Depth of penetration, 50 kg. (mm × 10⁻²) | Depth of penetration, 100 kg. (mm × 10⁻²) |
| 1 and 2: | as in Experiments 1 and 2 of Table I. | | | | | |
| Experiment 3: | Compound of Example 1; composition of Example 5 of Table 1 but with 0.6% of lauroyl peroxide and polymerization conducted at 160° C. for 0.5 hours. | | | | | |
| Experiment 4: | Compound of Example 11; composition of Experiment 10 of Table I. | | | | | |

The data in Table II demonstrate that the initial high breaking strength of the commercially available preparations is rapidly lost under the experimental conditions and the materials rapidly deteriorate. On the other hand, the compositions according to this invention are absolutely stable.

It has already been discussed hereinabove that a very important requirement for the application of synthetic materials to dental medicine is that the materials have no tendency to absorb water. For this reason, experiments were conducted to determine the changes in dimensions in the presence of water. As a measure of the absorption of water, the expansion in length under water at 36° C. was measured. The samples had length of 60 mm., width of 6 mm. and height of 2 mm. They were kept under water at 36° C. and the change in length was determined by optical measurements. The results are summarized in Table III below.

Table III

| Experiment No. | Monomer | Additive | Length of the test in days at 36° C. | Linear expansion in % |
|---|---|---|---|---|
| 1 | Compound of Example 1 | 120% Polymethyl-methacrylate "Plexigum M 353" 0.8% lauroyl peroxide | 126 | 0.02 |
| 2 | Compound of Example 1 | 100% Polymethyl-methacrylate "Kallocryl BPr" containing peroxide | 178 | 0.00 |
| 3 | Compound of Example 10 | 100% Polymethyl-methacrylate "Plexigum M 353" 0.6% lauroyl peroxide | 103 | 0.04 |
| 4 | Compound of Example 11 | 100% polymethyl-methacrylate "Plexigum M 353" 0.6% lauroyl peroxide | 96 | 0.13 |
| 5 | Triethyleneglycol-dimethacrylate commercially available preparations | 100% Polymethyl-methacrylate "Pyroplast" containing peroxide | 42 | 1.11* |

*Further measurements could not be taken because the samples were distorted.

Manifestly the compositions prepared according to this invention exhibited no tendency to pick up water, while the commercially known products underwent a substantial change in dimensions.

What is claimed is:

1. An artificial denture prepared by disposing in the configuration of said artificial denture and then polymerizing at least one essentially pure compound of the formula

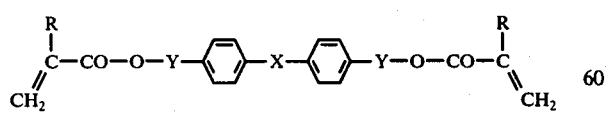

wherein R is hydrogen of methyl, X is an

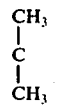

or the — SO₂ — group, Y is an oxyalkylene group of 2-5 carbon atoms or an alkylidene group of 2-3 carbon atoms.

2. An artificial denture according to claim 1, in which the compound polymerized is

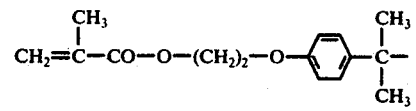

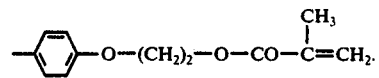

3. An artificial denture according to claim 1, in which the compound polymerized is

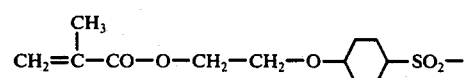

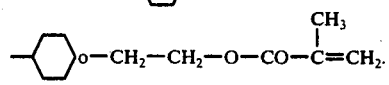

4. An artificial denture according to claim 1, in which the compound polymerized is

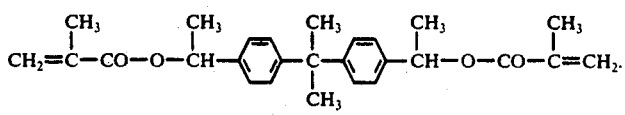

5. An artificial denture according to claim 1, in which the compound polymerized is

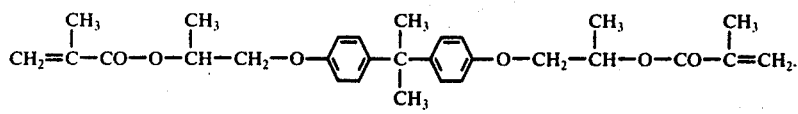

6. An artificial denture according to claim 1, in which the compound polymerized is

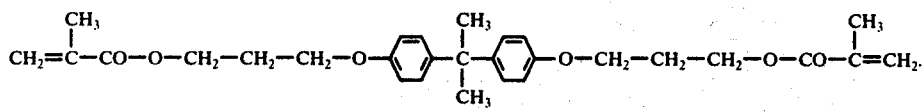

7. An artificial denture according to claim 1, in which the compound polymerized is

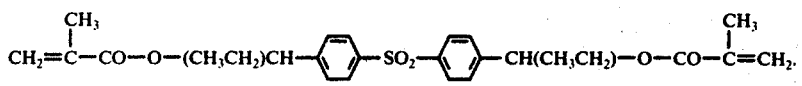

8. An artificial denture according to claim 1, in which the compound polymerized is

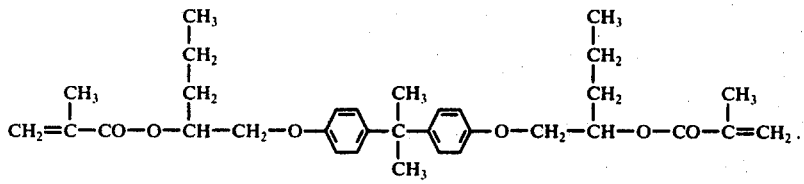

9. An artificial denture according to claim 1, in which the compound polymerized is

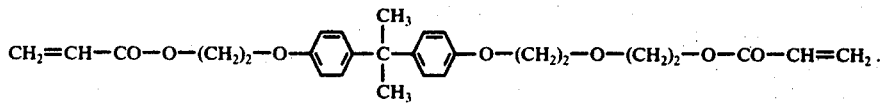

10. An artificial denture according to claim 1, in which X is the $SO_2$ group.

11. An artificial denture according to claim 1, in which the compound is polymerized in admixture with a filler.

12. An artificial denture according to claim 1, in which the filler is a member selected from the group consisting of glass fibers, quartz fibers, quartz powder, alumina and silicates.

* * * * *

UNITED STATES PATENT AND TRADEMARK OFFICE
CERTIFICATE OF CORRECTION

PATENT NO. : 4,067,853
DATED : January 10, 1978
INVENTOR(S) : Werner Schmitt, Robert Purrmann, Peter Jochum and Wolf Dieter Zahler.

It is certified that error appears in the above-identified patent and that said Letters Patent are hereby corrected as shown below:

Claim 3, the formula is corrected as follows:

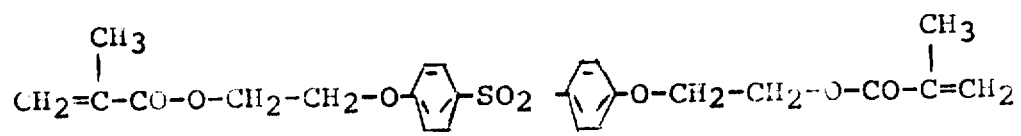

Claim 9, the correct formula is:

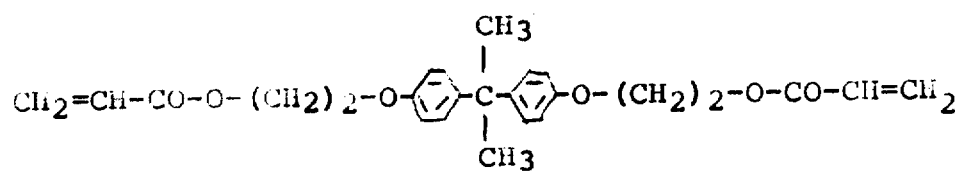

Signed and Sealed this

Thirtieth Day of May 1978

[SEAL]

Attest:

RUTH C. MASON
Attesting Officer

LUTRELLE F. PARKER
Acting Commissioner of Patents and Trademarks